(12) United States Patent
Yamazaki

(10) Patent No.: US 9,651,500 B2
(45) Date of Patent: May 16, 2017

(54) SIZING DEFECT DETECTION SYSTEM AND SIZING DEFECT DETECTION METHOD

(71) Applicant: YOSHINO GYPSUM CO., LTD., Tokyo (JP)

(72) Inventor: Masahiko Yamazaki, Tokyo (JP)

(73) Assignee: YOSHINO GYPSUM CO., LTD., Tokyo (JP)

( * ) Notice: Subject to any disclaimer, the term of this patent is extended or adjusted under 35 U.S.C. 154(b) by 0 days.

(21) Appl. No.: 14/895,662

(22) PCT Filed: May 23, 2014

(86) PCT No.: PCT/JP2014/063628
§ 371 (c)(1),
(2) Date: Dec. 3, 2015

(87) PCT Pub. No.: WO2014/208226
PCT Pub. Date: Dec. 31, 2014

(65) Prior Publication Data
US 2016/0123895 A1    May 5, 2016

(30) Foreign Application Priority Data
Jun. 24, 2013  (JP) .................................. 2013-131749

(51) Int. Cl.
*G01N 21/00* (2006.01)
*G01N 21/89* (2006.01)
(Continued)

(52) U.S. Cl.
CPC ............... *G01N 21/89* (2013.01); *B32B 3/04* (2013.01); *B32B 7/045* (2013.01); *B32B 7/12* (2013.01);
(Continued)

(58) Field of Classification Search
CPC . B32B 13/08; B32B 2250/44; B32B 2307/58; B32B 2307/718; B32B 2307/72;
(Continued)

(56) References Cited

U.S. PATENT DOCUMENTS

| 3,695,771 A | 10/1972 | Bardos |
| 4,284,357 A | 8/1981 | Kudo |

(Continued)

FOREIGN PATENT DOCUMENTS

| EP | 1132710 A1 | 9/2001 |
| JP | 5-346319 | 12/1993 |

(Continued)

OTHER PUBLICATIONS

International Preliminary Report on Patentability completed on Apr. 28, 2015 in related International Application No. PCT/JP2014/063628.

(Continued)

*Primary Examiner* — Tri T Ton
(74) *Attorney, Agent, or Firm* — Staas & Halsey LLP

(57) ABSTRACT

A light emission part projects a laser light toward an edge portion of a formation. The laser light extends in a direction intersecting a conveyance direction of a forming belt. A light receiving part is opposed to the light emission part and located on the opposite side of the formation. The laser light passes through an area above an upper surface of the formation at least partially and is partially blocked by rising of the edge portion of the formation. A control device determines occurrence of the glue-joint failure on the basis of whether the quantity of light received by the light receiving part is reduced by at least a predetermined value or a predetermined rate, and provides or gives a visual display or a warning of the occurrence of glue-joint failure.

19 Claims, 12 Drawing Sheets

(51) Int. Cl.
  *B32B 13/08* (2006.01)
  *G01N 21/95* (2006.01)
  *B32B 7/04* (2006.01)
  *B32B 7/12* (2006.01)
  *B32B 29/00* (2006.01)
  *B32B 3/04* (2006.01)
  *G01N 21/84* (2006.01)

(52) U.S. Cl.
  CPC ............ *B32B 13/08* (2013.01); *B32B 29/005* (2013.01); *G01N 21/8901* (2013.01); *G01N 21/95* (2013.01); *B32B 2250/44* (2013.01); *B32B 2307/58* (2013.01); *B32B 2307/718* (2013.01); *B32B 2307/72* (2013.01); *G01N 2021/845* (2013.01); *G01N 2021/8917* (2013.01); *G01N 2201/06113* (2013.01)

(58) Field of Classification Search
  CPC ......... B32B 29/005; B32B 3/04; B32B 7/045; B32B 7/12; G01N 2021/845; G01N 2021/8917; G01N 21/89; G01N 21/8901; G01N 21/95
  USPC ............... 356/237.1–237.6, 239.1–239.8
  See application file for complete search history.

(56) References Cited

U.S. PATENT DOCUMENTS

| | | |
|---|---|---|
| 6,144,038 A | 11/2000 | Gerstenberger et al. |
| 2002/0030319 A1 | 3/2002 | Komulainen et al. |
| 2013/0061777 A1 | 3/2013 | College et al. |

FOREIGN PATENT DOCUMENTS

| | | |
|---|---|---|
| JP | 6-171008 | 6/1994 |
| JP | 2000-74646 | 3/2000 |
| JP | 2003-293515 | 10/2003 |
| JP | 2008-184206 | 8/2008 |

OTHER PUBLICATIONS

Kisaku Furuya, "Recovery and Utilization of Gypsum", pp. 154-159, vol. 107, No. 2, 1991.
International Search Report mailed Jul. 22, 2014, in corresponding International Application No. PCT/JP2014/063628.
Extended European Search Report mailed Jan. 12, 2017 in related European Application No. 14817828.8.

Fig. 1
(A)
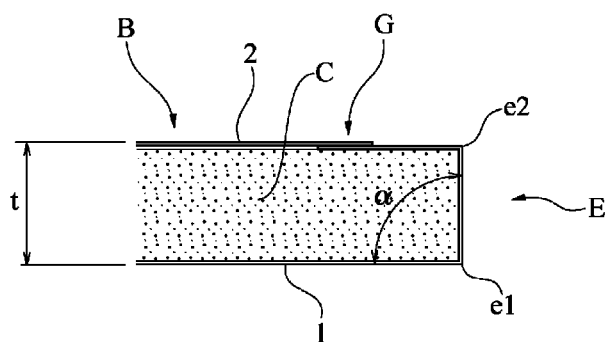
(B)
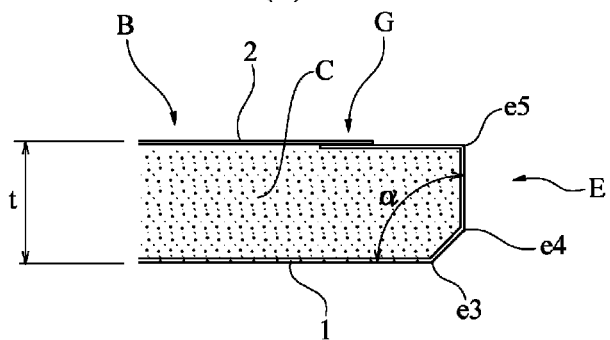
(C)
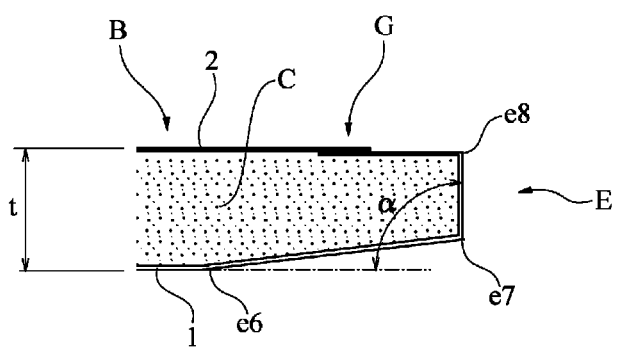

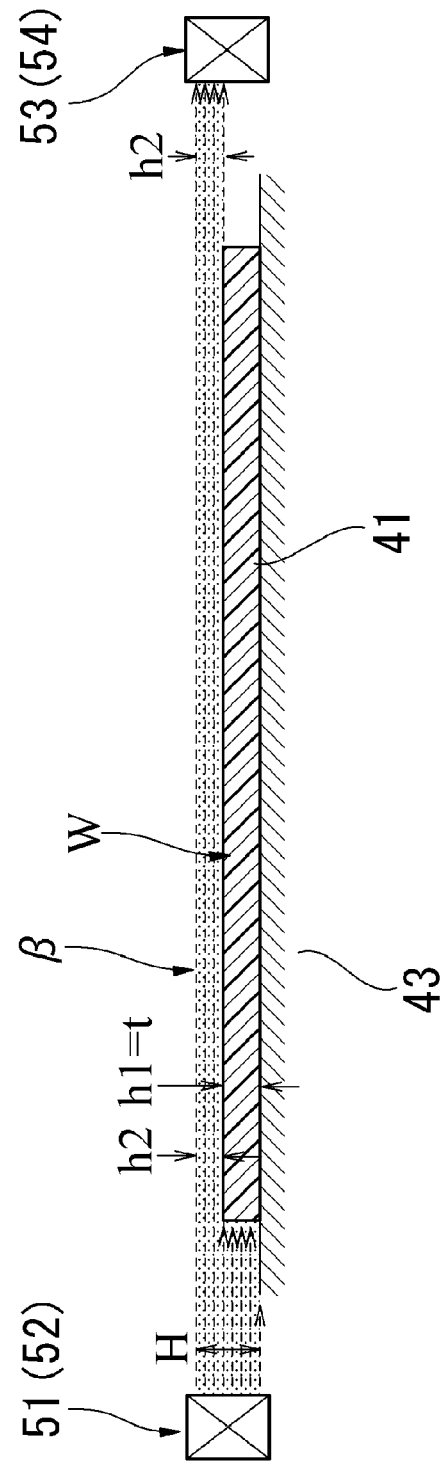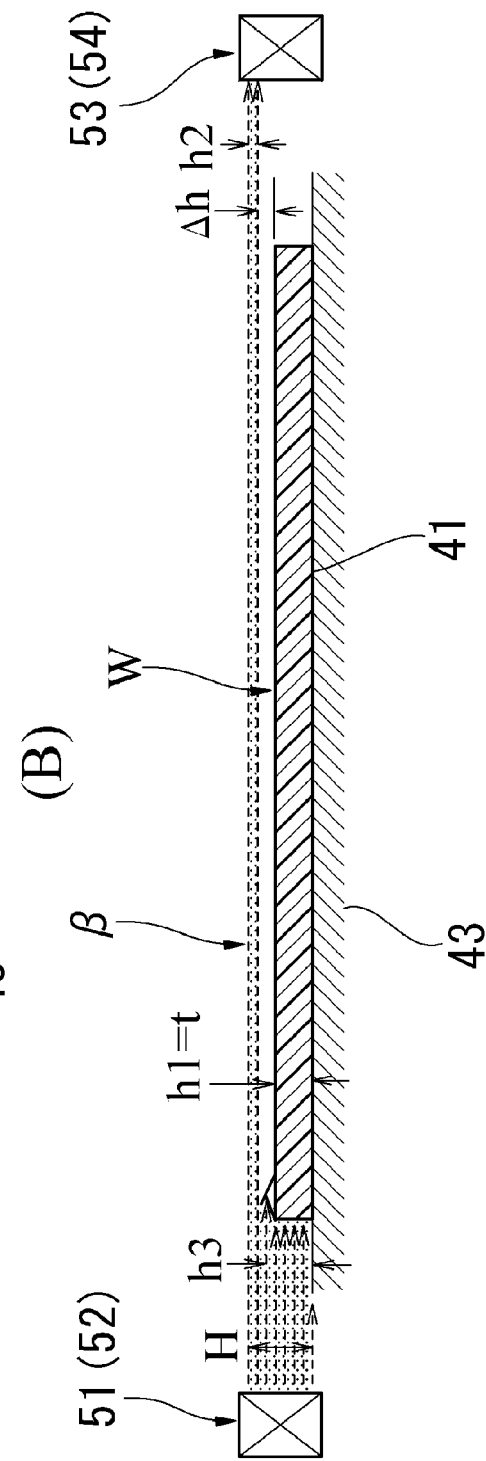
Fig. 6

Fig. 12
(A)
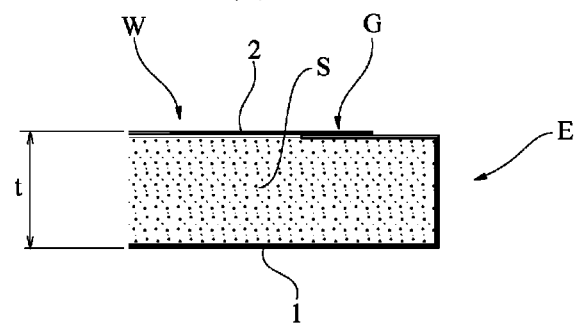
(B)
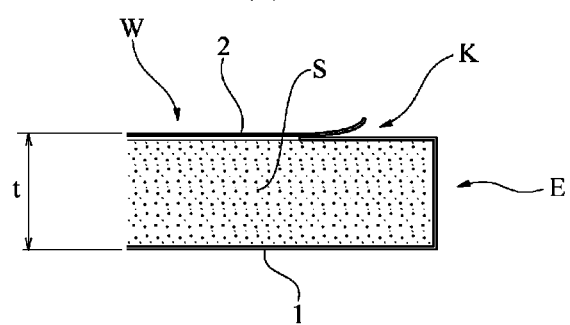
(C)
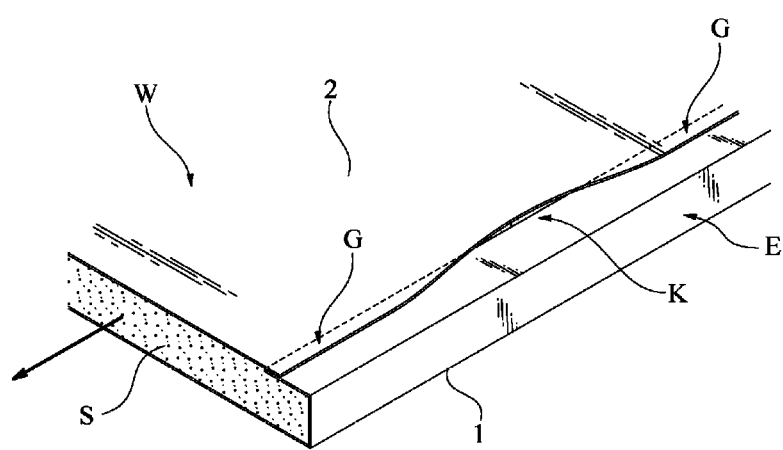

SIZING DEFECT DETECTION SYSTEM AND SIZING DEFECT DETECTION METHOD

CROSS-REFERENCE TO RELATED APPLICATIONS

This application is a U.S. National Stage Application, which claims the benefit under 35 U.S.C. 371 of PCT International Application No. PCT/JP2014/063628, filed May 23, 2014, which claims the foreign priority benefit under 35 U.S.C. 119 of Japanese Patent Application No. 2013-131749, filed on Jun. 24, 2013, the contents of which are incorporated herein by reference.

TECHNICAL FIELD

The present invention relates to an apparatus and method for detecting glue-joint failure, and more specifically, to such an apparatus and method which can detect the glue joint failure at a glue-joint section of sheets of paper for gypsum board liner in a process of producing gypsum boards.

TECHNICAL BACKGROUND

A gypsum board is known as a board which is constituted from a core mainly made from gypsum and sheets of paper for gypsum board liner covering the core. The gypsum boards are widely used in various kinds of buildings as architectural interior finish materials, because of their advantageous fire-resisting or fire-protecting ability, sound insulation performance, workability, cost performance and so on. In general, the gypsum boards are produced by a continuous slurry pouring and casting process. This process comprises a mixing step, a forming step and a drying and cutting step. In the mixing step, calcined gypsum, adhesive auxiliary agent, set accelerator, foam (or foaming agent), the other additives and so forth are mixed with admixtures and mixing water in a mixer. In the forming step, calcined gypsum slurry prepared in the mixer (referred to as "slurry" hereinafter) is fed into an area between upper and lower sheets of paper for gypsum board liner, so that a continuous plate-like and belt-like layered formation is formed. In the drying and cutting step, the continuous layered formation, which has dried and set to some extent on a conveyer device, is roughly severed and forcibly dried, and thereafter, cut to be a product size.

In such a process of producing the gypsum boards, the lower sheet of paper for gypsum board liner (referred to as the "lower sheet" hereinafter) is unwound from a paper roll of the sheet on a roll stand for the lower sheet. The lower sheet is continuously transferred by a forming belt (an upper belt track) of a belt conveyor device continuously moved. The slurry continuously discharged from the mixer is poured onto the lower sheet. A plurality of scores (creases or folding lines) are formed on right and left edge portions of the lower sheet by a scoring device, a grinding tool or the like, and then, the edge portions of the lower sheet are folded in line with the scores. On the other hand, the upper sheet of paper for gypsum board liner (referred to as the "upper sheet" hereinafter) is unwound from a paper roll of the sheet on a roll stand for the upper sheet, and the upper sheet is overlaid on the slurry. A gluing device, which applies or coats a quantity of glue to the right and left edge portions of the upper sheet immediately before the upper sheet is overlaid on the slurry, is provided on an apparatus for producing the gypsum boards. The gluing device includes a glue supply part which continuously applies or coats a predetermined quantity of glue to the edge portions of the upper sheet.

Each of the edge portions of the upper paper glued by the gluing device is aligned with each of the edge portions of the lower sheet and overlaid thereon, and the continuous three-layered formation comprising the upper and lower sheets and the slurry is fed to a forming device, such as forming plates or forming rollers. The continuous three-layered formation shaped in a form of plate-like continuous strip by the forming device is continuously transferred by the belt conveyer device, and it dries and sets to some extent thereon, and then, it is roughly severed, and thereafter, forcibly dried by a drying device for removing excessive water and cut to be the product size.

FIG. 12 includes partial cross-sectional views and a partial perspective view, each illustrating a structure of the edge portion of the aforementioned continuous layered formation W which has the upper and lower sheets 1, 2 glued. In FIG. 12(A), a cross-section of the edge portion suitably glued. In FIGS. 12(B) and 12(C), a configuration of the edge portion is shown in which a glue joint failure occurs.

When the upper and lower sheets are desirably joined together at a glue joint section G as shown in FIG. 12(A), an edge portion E with a rectangular cross-section is made, which encloses the slurry S in a state before drying and setting. The continuous layered formation W having a thickness t is conveyed in a conveyance direction of the forming belt, as shown by an arrow in FIG. 12(C). As illustrated as an exfoliation or gap K in FIGS. 12(B) and 12(C), the edge portion of the upper paper 2 may be partially separated from the edge portion of the lower paper 1, owing to an incomplete joint at the glue joint section G. Such an exfoliation K may occur immediately after gluing, or may occur during the drying and setting process of the slurry S. The exfoliation K slightly appearing immediately after gluing sometimes rejoins naturally, during the drying and setting process of the slurry S. Therefore, it is very difficult to locate the position where the exfoliation K occurs in the production line.

Further, such an exfoliation K tends to occur frequently in the production line for producing the gypsum boards with a high specific gravity equal to or greater than 0.9, compared to the production line for producing the gypsum boards with a standard specific gravity which is smaller than 0.9. Taking its cause into consideration, this is because a relatively thick paper with a large basis weight is used for the gypsum boards with high density and a weight or load of the slurry with high density acts on the lower and upper sheets.

Furthermore, also in a case of production of the light-weight gypsum boards having the specific gravity smaller than the specific gravity (the specific gravity in a range of 0.7 to 0.8) of the standard gypsum boards (referred to as the "light-weight gypsum boards" hereinafter), the paper with a heavy weight may be used for ensuring strength of the entire gypsum board. In a case where the light-weight gypsum boards are produced with use of such paper, the glue-joint failure may occur relatively frequently.

The gypsum board products with the exfoliations K remaining thereon have to be removed from the product line, as being irregular products or defective products which cannot be shipped. This results in increase of production loss and deterioration of production yield. For improvement of the yield of production in the gypsum board production process, it is desirable to surely detect the glue joint failure at an early stage, thereby eliminating or overcoming the cause of the glue-joint failure at the early stage, by means of adjustment or regulation of the gluing device.

In Japanese Patent Laid-Open Publication No. 2000-74646 (Patent Literature 1), a device for detecting an edge angle is disclosed, which detects an angle of an edge face (a side end face) with use of an optical detection means, in order to detect a defective shape-forming at the edge portion of the gypsum board. This device comprises a light source for laser light or the like, a CCD image capturing device, an image processing device, and so forth. The light source continuously irradiates the side edge zone of the aforementioned continuous layered formation with light for imaging, and the image capturing device receives the light reflected from the side edge zone and continuously captures the image of the edge portion. The image processing device carries out image processing of the image of the edge face to measure an apparent width of the edge, and detects the edge angle on the basis of the measured width of the edge.

In Japanese Patent Laid-Open Publication No. 5-346319 (Patent Literature 2), a surface inspection device is disclosed, which is intended to detect failures occurring on an edge portion or a surface of the aforementioned continuous layered formation, by means of optical detection means. This inspection device has a light projector and a light receiving device. The light projector emits linear or plane light toward the edge portion or the surface of the continuous layered formation for visually representing a bright line or pattern on the edge portion or the surface. The light receiving device receives the light reflected from the continuous layered formation to form an image of the bright line or pattern on the formation, and detects an inclination or variation of the bright line or pattern appearing on the edge portion or the surface by means of arithmetic processing or numerical analysis.

CITATION LIST

Patent Literatures

[Patent Literature 1] Japanese Patent Laid-Open Publication No. 2000-74646
[Patent Literature 2] Japanese Patent Laid-Open Publication No. 5-346319

SUMMARY OF INVENTION

Technical Problem

However, the device for detecting the defective edge angle (Patent Literature 1 (JP 2000-74646)) cannot detect the glue-joint failure of the upper and lower sheets. Even if it is assumed that the device may detect change or variation of the edge angle in association with the glue joint failure, it is not possible to determine whether this change or variation results from the glue-joint failure. Therefore, the device for detecting the defective edge angle as disclosed in Patent Literature 1 cannot detect the glue joint failure.

On the other hand, according to the surface inspection device of JP 5-346319 (Patent Literature 2) which optically represents the bright line or pattern on the edge portion or the surface of the continuous layered formation and detects the inclination or variation of the bright line or pattern, it might be possible to detect abnormality of the continuous layered formation on the basis of variation of the pattern. However, it is not possible to determine whether such abnormality results from the glue joint failure, and therefore, the glue-joint failure cannot be detected by the surface inspection device of Patent Literature 2.

Further, the device of each of Patent Literatures 1 and 2 is arranged to continuously emit the light for imaging from the light source or the light projector to the continuous layered formation, whereby the light reflected from the continuous layered formation forms an image on an image forming part of the image capturing device or the light receiving device. Therefore, it is necessary to ensure an environment or condition for discriminating between the reflected light deriving from the light for imaging and the reflected light deriving from natural or artificial light existing in a manufacturing site. For such a reason, the device of each of Patent Literatures 1 and 2 requires installation of a relatively large-scale blackout curtain or the like surrounding a detecting or inspecting system, in order to prevent the natural or artificial light of the manufacturing site or environment from affecting the inspected part, thereby allowing the reflected light to be clearly visible or imagable. However, in practice, it is difficult to carry out installation of such blackout curtain or the like, in view of the construction and scale of the gypsum board production apparatus.

Furthermore, the exfoliation at the glue joint section (the exfoliation K in FIG. 12) occurs not only immediately after gluing, but also during the drying and setting process of the slurry. In addition, the exfoliation occurring immediately after gluing may naturally rejoin during the drying and setting process of the slurry. Therefore, it is very difficult to predict where the exfoliation occurs in the production line, and it is preferable that the glue joint failure is detected at a plurality of points in the production line. However, if the plurality of detection or inspection devices (Patent Literatures 1 and 2), each being arranged to radiate the light for imaging on the continuous layered formation and each forming the image by the reflected light, are provided on the gypsum board production apparatus, the structure of the apparatus would become complicated and the initial cost and investment for constructing the apparatus would be increased.

It is an object of the present invention to provide a system and method for detecting the glue joint failure, which can surely detect the glue joint failure of the upper and lower sheets at an early stage with a simple arrangement, and which allows a plurality of detecting equipment systems to be relatively easily provided in positions of the gypsum board production line, spaced apart a distance in the conveyance direction of the continuous layered formation.

Solution to Problem

The present invention provides a system for detecting glue joint failure, which is provided on a gypsum board production apparatus and which detects the glue-joint failure at a glue joint section of upper and lower sheets of paper for gypsum board liner with use of optical detection means, wherein the gypsum board production apparatus is arranged to glue edge portions of the sheets with gypsum slurry being fed between the sheets, thereby forming a continuous layered formation, which is formed with a cross-section of an edge portion of a gypsum board and which is conveyed by a forming belt, comprising:

a light emission part which is located on one side of said continuous layered formation and which projects a laser light toward an edge portion of said formation, the laser light extending in a direction intersecting a conveyance direction of the forming belt;

a light receiving part which is opposed to the light emission part and located on the opposite side of said formation and which receives the laser light of the light emission part; and a control device for determining occurrence of the glue-joint failure when a height of said laser light blocked by said formation exceeds a predetermined value or a predetermined rate, wherein said laser light is so positioned that the laser light at least partially passes through an area above an upper surface of said formation and is partially blocked by rising of the edge portion of the formation.

The present invention also provides a method for detecting glue joint failure at a glue joint section of upper and lower sheets of paper for gypsum board liner with use of optical detection means, wherein the optical detection means is provided on a gypsum board production apparatus arranged to glue edge portions of the sheets with gypsum slurry being fed between the sheets, thereby forming a continuous layered formation, which is formed with a cross-section of an edge portion of a gypsum board and which is conveyed by a forming belt, comprising steps of:

projecting a laser light extending in a direction intersecting a conveyance direction of the forming belt, toward the edge portion of said formation, by means of a light emission part located on one side of the formation;

positioning said laser beam so that the laser light at least partially passes through an area above an upper surface of said formation and is partially blocked by rising of the edge portion of the formation;

receiving the laser light of said light emission part by means of a light receiving part which is opposed to the light emission part and located on the opposite side of said formation; and measuring a quantity of light received by said light receiving part and determining occurrence of the glue-joint failure on the basis of whether the quantity of light decreases by at least a predetermined value or a predetermined rate.

In experiments of the present inventor, rising of the glue-joint section of the upper and lower sheets tends to be generated to the extent of at least 5-10% of the thickness of the continuous layered formation (the thickness of the gypsum board), or to the extent of the percentage equal to or greater than 10% thereof, when the glue-joint failure happens at the edge portion. According to the aforementioned arrangement of the present invention, the laser light passes at least partially in the area above the upper surface of the continuous layered formation, and is received by the light receiving part. When the rising of the edge portion occurs, the laser light is partially blocked by the rising of the edge portion of the continuous layered formation. Therefore, the occurrence of the glue-joint failure can be surely determined at an early stage by detecting the quantity of the light or the rate of the light blocked by the continuous layered formation, and a visual display or warning of the occurrence of the glue-joint failure can be provided or given to an operator and so forth. The operator and so forth can eliminate the glue joint failure promptly at an early stage by adjustment or regulation of the gluing device, which can be preformed on the basis of the visual display or the warning of the glue-joint failure. Therefore, a lot of defective products can be prevented from being produced, and the yield of production can be improved.

In the experiments of the present inventor, exfoliation of the glued section happens not only immediately after gluing, but also during the drying and setting process of the slurry on the forming belt, and therefore, it is preferable to detect the glue joint failure in a plurality of positions of the gypsum board production line. According to the aforementioned arrangement of the present invention, a detecting equipment system constituted from the light emission part and the light receiving part in a pair can be located in an arbitrary position of the gypsum board production line, and therefore, the plurality of detecting equipment systems can be relatively easily located in proper and spaced positions of the production line. Thus, the plurality of detecting equipment systems for detecting the glue-joint failure in the plurality of positions of the production line can be relatively easily provided in the production line, spaced apart a distance from each other.

From another aspect, the present invention provides an apparatus for producing the gypsum boards having the aforementioned system. Preferably, the apparatus has a lower sheet feeding device for feeding to the lower sheet conveyance line, the lower sheet with its basis weight being in a range from 170 $g/m^2$ to 300 $g/m^2$ (e.g., the lower sheet having a thickness equal to or greater than 0.3 mm (equal to or smaller than 0.4 mm) and the basis weight of 200 $g/m^2$).

From yet another aspect, the present invention provides a method for producing the gypsum boards with use of the aforementioned method for detecting the glue-joint failure. Preferably, a lower sheet with its basis weight being in a range from 170 $g/m^2$ to 300 $g/m^2$ (e.g., the lower sheet having a thickness equal to or greater than 0.3 mm (equal to or smaller than 0.4 mm) and the basis weight of 200 $g/m^2$) is used as a raw material, and the gypsum boards with high density, which have a specific gravity equal to or greater than 0.9, are produced, or the light-weight gypsum boards, which have a specific gravity equal to or less than 0.6, are produced.

Advantageous Effects of Invention

According to the present invention, the system and method for detecting the glue-joint failure can be provided, which can surely detect the glue-joint failure of the upper and lower sheets at an early stage with a simple arrangement, and which allows a plurality of detecting equipment systems to be relatively easily provided in positions of the gypsum board production line, spaced apart a distance in the conveyance direction of the continuous layered formation.

BRIEF DESCRIPTION OF THE DRAWINGS

FIG. 1A to FIG. 1C includes partial cross-sectional views of gypsum boards, in which various kinds of edge configurations of the gypsum boards are illustrated.

FIG. 6A to FIG. 6B includes schematic cross-sectional views illustrating the concept of the system for detecting the glue-joint failure in the production process of the gypsum boards having a thickness of 12.5 mm.

FIG. 12A to FIG. 12C includes partial cross-sectional views and a partial perspective view exemplifying a structure of the edge portion of the continuous layered formation with the upper and lower sheets being glued, wherein FIG. 12(A) illustrates a cross-section of the edge portion suitably glued and FIGS. 12(B) and 12(C) illustrates a configuration of the edge portion with the glue-joint failure occurring.

DESCRIPTION OF EMBODIMENTS

Figure 2:
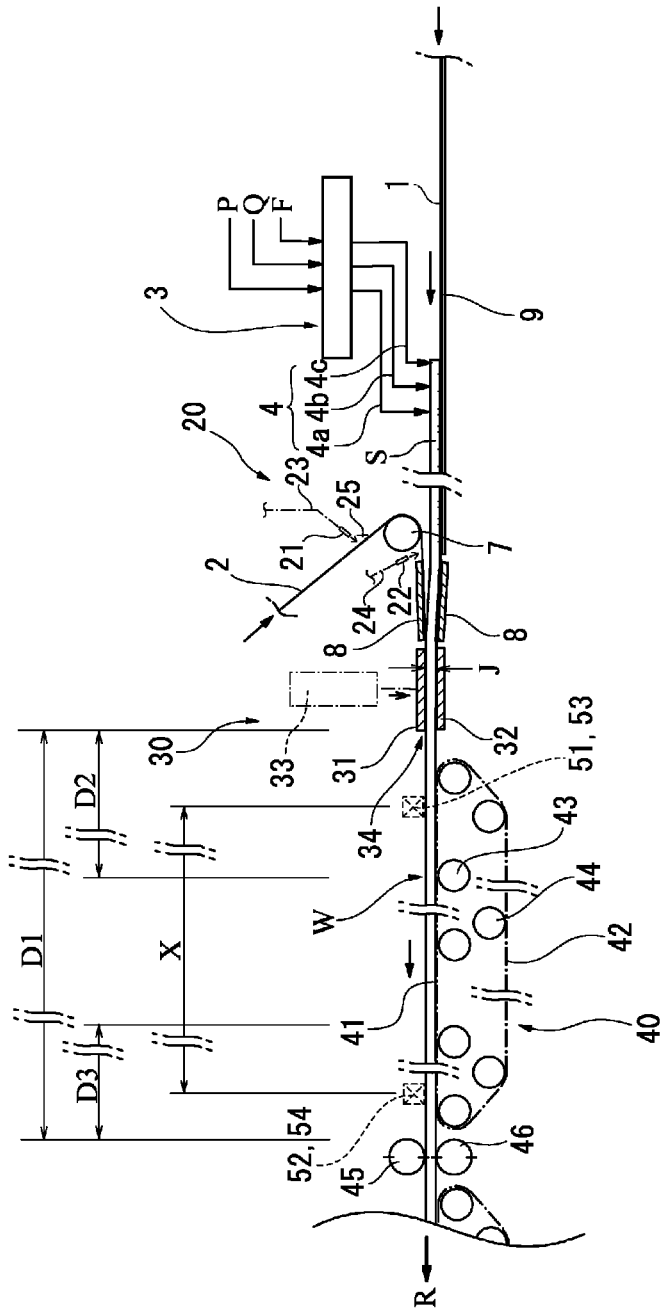
FIG. 2 is a partial cross-sectional view of a gypsum board production apparatus, in which a forming process of the gypsum boards is partially and schematically illustrated.

According to a preferred embodiment of the present invention, the plurality of light emission parts are in positions spaced apart from each other in the conveyance direction of a forming belt, the plurality of light receiving parts are in positions spaced apart from each other in the conveyance direction of the forming belt, and the plurality of laser lights are projected to the continuous layered formation in upstream and downstream areas of the forming belt respectively. Preferably, each of the laser lights has a horizontal optical axis perpendicular to the conveyance direction of the forming belt.

The system for detecting the glue-joint failure provides or gives information (visual display or warning) of the occurrence of the glue joint failure by visual or auditory information means, such as visual display means or warning means, when the occurrence of the glue-joint failure is determined on the basis of the quantity of light detected by at least one of the light receiving parts. Alternatively, the system provides or gives the visual display or warning of the occurrence of the glue-joint failure by the visual display means or warning means, when the occurrence of the glue joint failure is indicated by every result which is determined on the basis of the quantities of light detected by the light receiving parts.

Preferably, the quantity of light received by the light receiving part is input into a control device, as being a measured value. The quantity of light to be received in a normal condition by the light receiving part is set to be a reference value by the control device. The measured value of the quantity of light detected by the light receiving part is compared with the reference value by the control device, so that the occurrence of the glue-joint failure is determined. The quantity of light to be received in the normal condition by the light receiving part is, for example, preset on the basis of a thickness of the gypsum board before a start of production of the gypsum board, or otherwise, initially set or reset on the basis of the quantities of light constantly received by the light receiving part after the start of production of the gypsum board. The system provides or gives the visual display or warning of the occurrence of the glue-joint failure by the visual display means or warning means, when the quantity of light measured by the light receiving part decreases down to a predetermined rate of the reference value or less. Preferably, this rate is set to be in a range from 95% to 85%, e.g., 90%. This rate or ratio may be changed in accordance with the thickness of the gypsum board, the sort thereof, or the like.

In a preferred embodiment, the control device comprises an arithmetic and control part, a memory part, and a comparison and discrimination part. The comparison and discrimination part controls operation of the light emission part and the light receiving part, and receives a detected result of the light receiving part to compute the measured value of the quantity of received light. The memory part memorizes the quantity of light to be received in a normal condition by the light receiving part, as being a reference value, and memorize a threshold for determining the occurrence of the glue-joint failure, which is set on the basis of the reference value. The comparison and discrimination part compares the measured value and the reference value to determine the occurrence of the glue-joint failure. Preferably, the control device further comprises means for providing or giving the visual display or warning of the occurrence of the glue-joint failure when the comparison and discrimination part determines the occurrence of the glue-joint failure.

Embodiment

With reference to the attached drawings, a preferred embodiment of the present invention are described hereinafter.

FIG. 1 includes partial cross-sectional views of gypsum boards, in which various kinds of edge configurations of the gypsum boards are illustrated.

A gypsum board B with a thickness t has a structure in which a gypsum core C is covered with upper and lower sheets of paper for gypsum board liner, i.e., a lower sheet 1 and an upper sheet 2, wherein the core C is a solidified matter of gypsum slurry. FIG. 1(A) shows the board B having an edge portion in a form of "square edge". An edge portion is formed at an edge angle α which is set to be a right angle. The sheet 1 is folded at corners e1, e2. An edge portion of a back face of the sheet 2 (the edge portion of its lower face in FIG. 1), to which glue is applied or coated, is overlaid on an upper face of an edge portion of the sheet 1, whereby a glue joint section G is formed. FIG. 1(B) shows the board B having the edge portion in a form of "beveled edge". The sheet 1 is folded at corners e3, e4, e5. The edge portion of the back face of the sheet 2, to which the glue is applied or coated, is overlaid on the upper face of the edge portion of the sheet 1, whereby the glue joint section G is formed. FIG. 1(C) shows the board B having the edge portion in a form of "tapered edge". The sheet 1 is folded at corners e6, e7, e8. The edge portion of the back face of the sheet 2, to which the glue is applied or coated, is overlaid on the upper face of the edge portion of the sheet 1, whereby the glue joint section G is formed.

Figure 3:
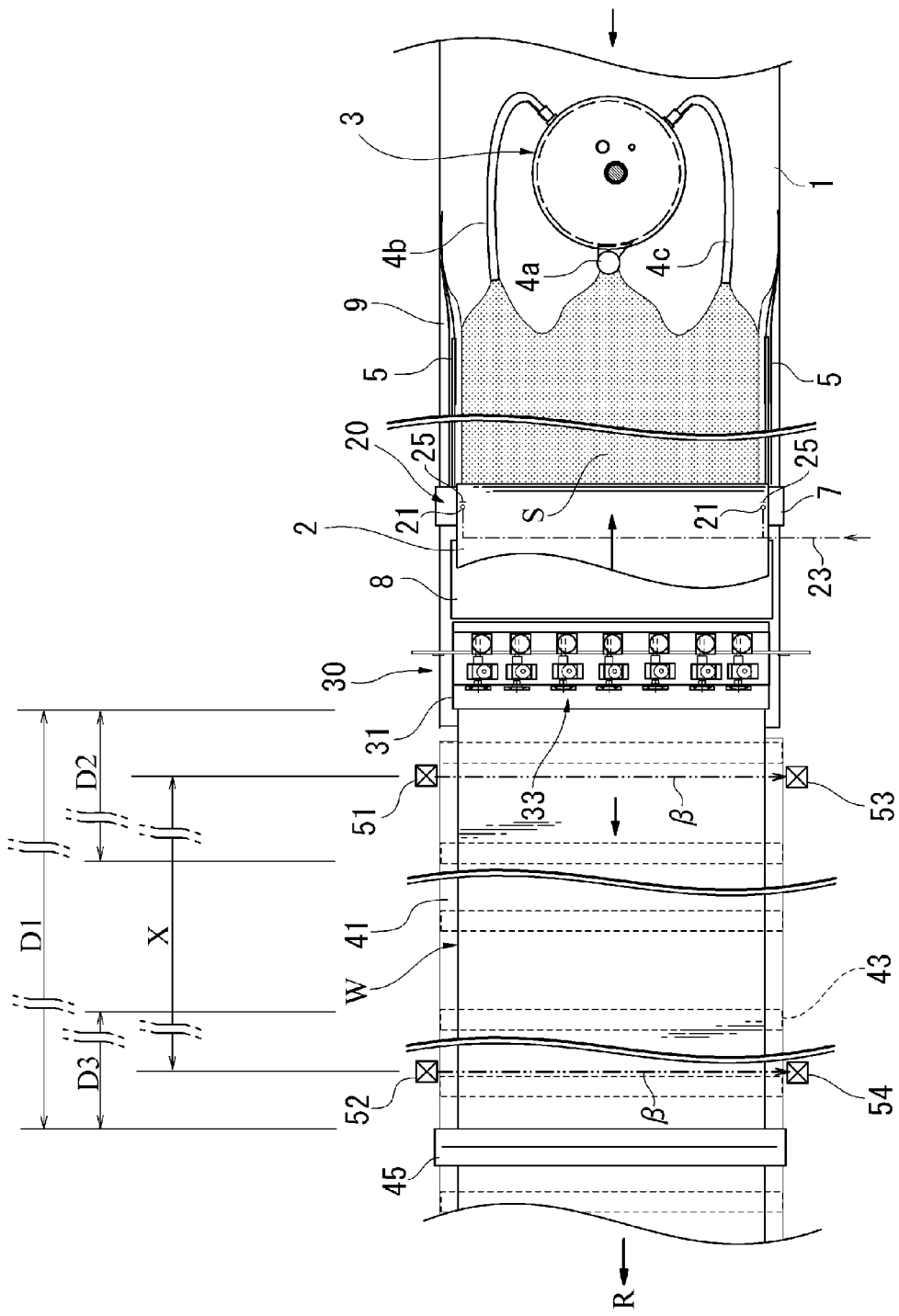
FIG. 3 is a plan view of the gypsum board production apparatus, in which the forming process of the gypsum boards is partially and schematically illustrated.

FIGS. 2 and 3 are a partial cross-sectional view and a partial plan view of a gypsum board production apparatus, in which a forming process of the gypsum boards are partially and schematically illustrated.

The sheet 1, which is unwound from a paper roll on a roll stand for the lower sheet (not shown), is supplied to a paper feed table 9 of the gypsum board production apparatus, and the sheet 1 is conveyed in a direction of a production line. Scores are made on the sheet 1 by a scoring device or a grinding device (not shown). For example, the scores are provided in positions corresponding to the corners e1, e2, in a case of the square edge. A mixer 3 is located in a position above a lower sheet conveyance line. Powder materials P (calcined gypsum, adhesive agent, set accelerator, additives, admixture and so forth), foam F and liquid (water) Q are fed to the mixer 10. The mixer 10 mixes these materials and discharges slurry (calcined gypsum slurry) S onto the sheet 1 by means of a tubular passages 4 (4a, 4b, 4c). The passage 4a discharges onto a widthwise center area of the sheet 1, the slurry S with relatively low density. Each of the passages 4b, 4c discharge onto each of edge portions of the sheet 1 (edge areas thereof), the slurry S with relatively high density. The sheet 1 is moved together with the slurry S on the production line, and the edge portions of the sheet 1 is folded upward by guide members 5.

The sheet 2, which is unwound from a paper roll on a roll stand for the upper sheet (not shown), is fed onto the slurry S by means of a feed roller 7. A gluing device 20 for applying or coating a predetermined quantity of glue to edge portions of the sheet 2 is positioned in proximity to the roller 7. The gluing device 20 is provided with a glue supply device 21 which continuously supplies the glue to the edge portion of the back face of the sheet 2 from its upper side. A glue supply source (not shown) is connected to the device 21 through a glue supply tube 23.

The sheet 1, the slurry S and the sheet 2 are layered by upper and lower surface plates 8 and pass through a gypsum board forming device 30 as a continuous three-layered formation W. The forming device 30 is provided with upper and lower horizontal plates 31, 32. The lower plate 32 is fixed to a frame (not shown) of the gypsum board production apparatus so as to transfer the sheet 1 horizontally. A lifting and lowering device 33 is located above the upper plate 31, spaced apart therefrom. The device 33 is connected with the plate 31. The level of the plate 31 is finely adjusted by the device 33. The height J (the gate dimension) of a forming gate 34 formed between the plates 31, 32 is strictly managed so that an appropriate forming pressure acts on the continuous layered formation W of the sheets 1, 2 and the slurry S. The continuous layered formation W passes through the gate 34 so as to be shaped as a continuous belt-like plate form having a desired thickness t (FIG. 1).

The continuous layered formation exiting the gate 30 is transferred to the following step (a roughly severing step) by an upper belt track 41 of a forming belt 40 constituting a belt conveyer device, and a setting reaction of the slurry proceeds on the belt 40. Roughly severing rollers 45, 46 roughly severs the continuous belt-like layered formation in which the setting reaction of the slurry has proceeded, whereby plates having a gypsum core covered by the sheets of paper for gypsum board liner, that is, green boards for the gypsum boards are produced. The green boards are passed through a dryer (shown by an arrow R in FIGS. 1 and 2) and forcibly dried therein, and thereafter, they are cut to be a product size, and thus, the gypsum board products are produced.

Laser light emitting sensors 51, 52 and laser light receiving sensors 53, 54 on upstream and downstream sides of the production line are positioned outside of the forming belt 40, wherein the sensors 51-54 constitute a system for detecting a glue-joint failure 50. The forming device 30 and the roughly severing rollers 45, 46 are spaced apart a distance D1 from each other. The sensors 51, 53 on the upstream side are provided in a pair and are positioned in a region of a distance D2 (D2=D1/4). This region is referred to as an "upstream region" hereinafter. The sensors 52, 54 on the downstream side are provided in a pair and are positioned in a region of a distance D3 (D3=D1/4). This region is referred to as a "downstream region" hereinafter. The pair of sensors 51, 53 in the upstream region and the pair of sensors 52, 54 in the downstream region are spaced apart a distance X in a conveyance direction, from each other.

Figure 4:
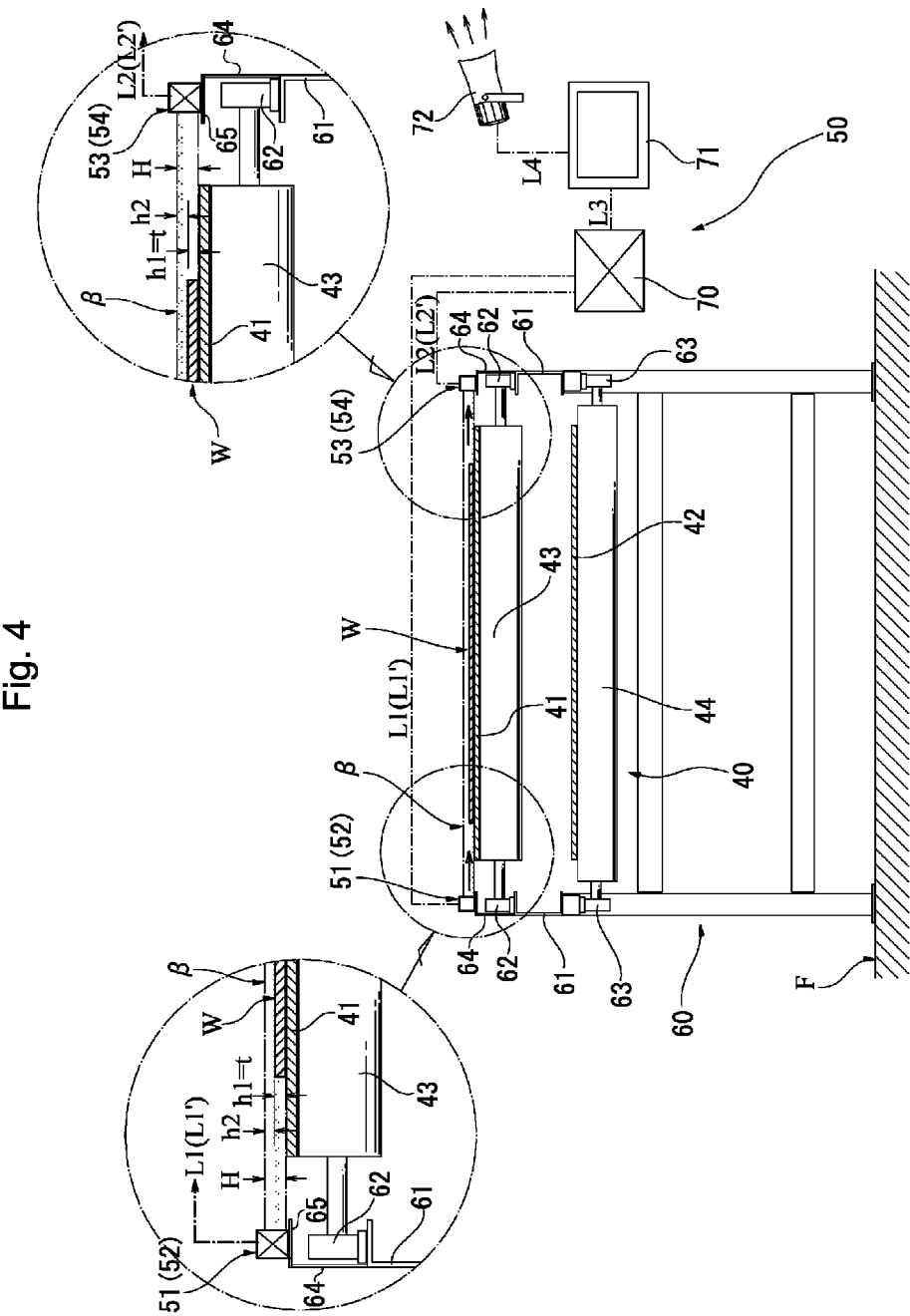
FIG. 4 is a cross-sectional view of the gypsum board production apparatus, which shows a positional relationship between light emission and light receiving sensors on an upstream side and a continuous layered formation.

FIG. 4 is a cross-sectional view of the gypsum board production apparatus, which shows a positional relationship between the sensors 51, 53 in the upstream region and the continuous layered formation W. As shown by reference numerals placed between parentheses in FIG. 4, an arrangement of the sensors 52, 54 in the downstream region is substantially the same as that of the sensors 51, 53 in the upstream region.

Bearings 62, 63 are mounted on right and left horizontal members 61 constituting a machine frame 60 of the gypsum board production apparatus. Upper and lower driven rollers 43, 44 of the belt conveyor device are rotatably carried by the bearings 62, 63. The forming belt 40 is an endless belt constituting the upper belt track 41 and the lower belt track 42. The belt 40 is installed on a number of rollers 43, 44 and drive rollers (not shown). The belt conveyor device has a driving device which rotates the drive rollers for moving the upper belt track 41 in the conveyance direction and moving the lower track 42 conversely.

Brackets 64 having sensor carriers 65 are provided on upper surfaces of the horizontal members 61. The sensor 51 is mounted on the carrier 65 on one side (on the left side in FIG. 4), and the sensor 53 is mounted on the carrier 65 on the opposite side (on the right side in FIG. 4). The sensor 51 emits a visible semiconductor laser beam β having a predetermined height H. The laser beam β has a horizontal optical axis perpendicular to the conveyance direction of the continuous layered formation W. The sensor 53 is provided with a light receiving part opposed to a light emission part of the sensor 51. When the continuous layered formation W does not exist on the upper belt track 41, the sensor 53 entirely receives the laser beam β of the predetermined height H which is a laterally thin and vertically long strip-like beam. In this embodiment, a lower edge of the laser beam β is positioned on the same level as the level of an upper surface of the upper belt track 41, and the height H of the laser beam β is set to be 30 mm. In a plan view (FIG. 3), the laser beam β is a ray of light in a form of a thin straight line, the width of which is negligible (the dimension of the laser beam β in the conveyance direction of the continuous layered formation W is negligible).

The sensors 51, 53 are connected with a control unit 70, e.g., a programmable logic controller (PLC), by means of control signal lines L1, L2. The control unit 70 has an arithmetic and control part, a memory part, a comparison and discrimination part, and a driver part. The arithmetic and control part controls operations of the sensors 51-54 and receives outputs (detection signals) of the sensors 53, 54. The quantities of light, which the sensors 53,54 receive in a normal condition, are stored as reference values by the memory part. The quantities of light detected by the sensors 53, 54 are also stored by the memory part. Further, the quantities of light, which correspond to 90% of the quantities of light (the reference values) received by the sensors 53,54 in a normal condition, are stored as thresholds for discrimination by the memory part. The comparison and discrimination part compares the measured values and the reference values on the basis of the thresholds, thereby determining whether the glue-joint failure occurs. The driver part controls operations of a touch panel display device 71, an electronic sound alarm 72 and so forth which constitute HMI (Human-Machine Interfaces).

The control unit 70 is connected with the display device 71 by means of a control signal line L3. The display device 71 is connected with the alarm 72 by means of a control signal line IA. As shown by reference numerals placed between parentheses in FIG. 4, the sensors 52, 54 in the downstream region are also connected with the control unit 70 by means of the control signal lines L1', L2'. The control unit 70, the display device 71 and the alarm 72 constitute a control device or control system in the system for detecting the glue joint failure 50.

Figure 5:
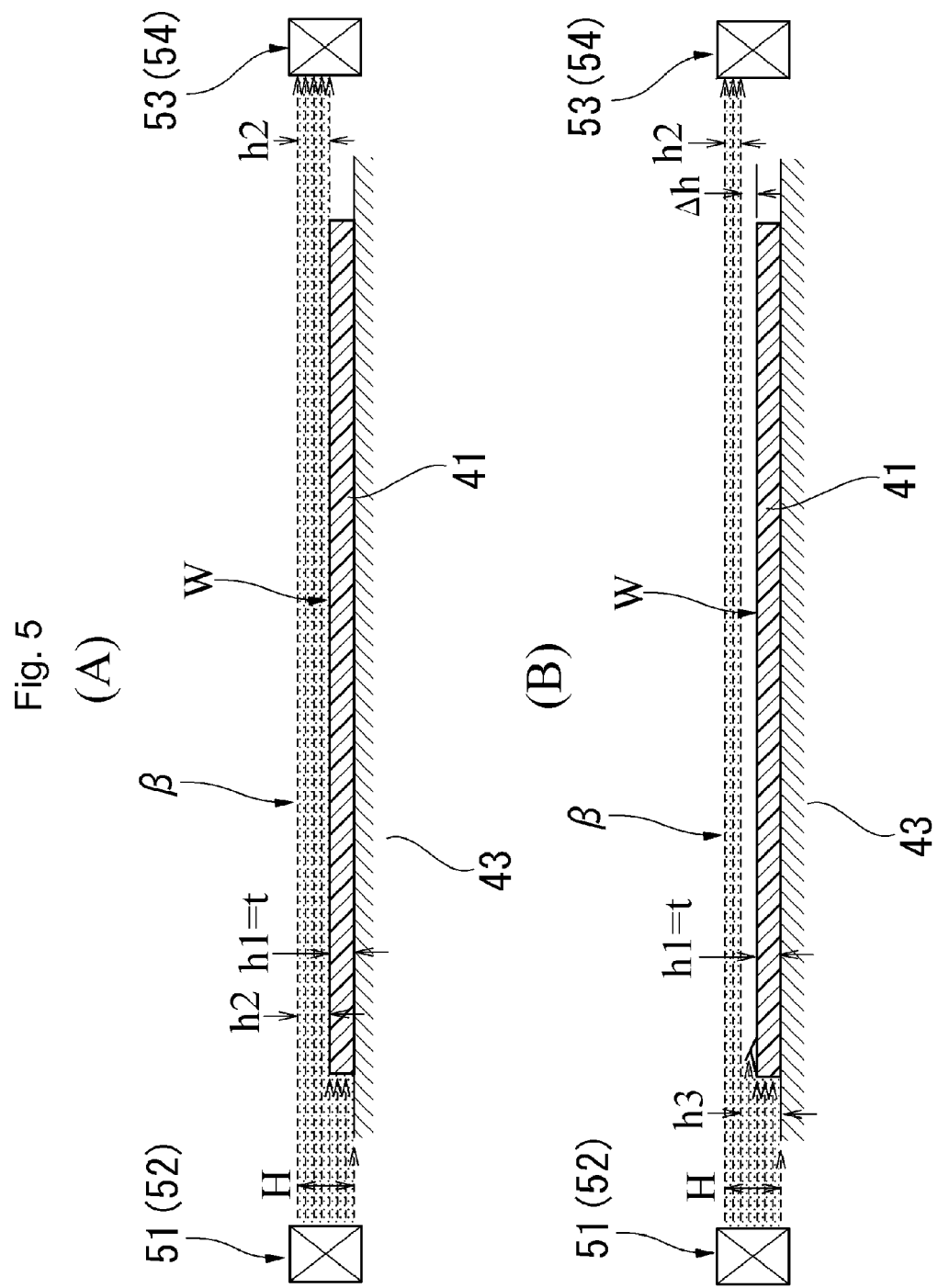
FIG. 5A to FIG. 5B includes schematic cross-sectional views illustrating a concept of a system for detecting the glue-joint failure in the production process of the gypsum boards having a thickness of 9.5 mm.

FIGS. 5 and 6 are schematic cross-sectional views illustrating a concept of the system for detecting the glue joint failure 50.

FIG. 5(A) shows a state in which the continuous layered formation W for producing the gypsum boards having a thickness t of 9.5 mm, is placed on the upper belt track 41. FIG. 6(A) shows a state in which the continuous layered formation W for producing the gypsum boards having a thickness t of 12.5 mm, is placed on the upper belt track 41. In a case where the continuous layered formation W has the glue-joint section G (FIG. 1) properly glued, the height h1 of the continuous layered formation W is coincident with the thickness t of the gypsum board. When the height H of the laser beam β is set to be 30 mm, the thickness h2 of the laser beam β received by the light receiving part of the sensor 53 is theoretically h2=H−h1=20.5 mm (FIG. 5(A)) or 17.5 mm (FIG. 6(A)), wherein measuring errors are neglected. The memory part of the control unit 70 stores the quantities of light received in normal conditions by the sensor 53 (54), as the reference values.

On the other hand, when the glue joint failure occurs at the glue-joint section G, the edge portion of the upper sheet 2 is raised as shown in FIGS. 5(B), 6(B), 12(B) and 12(C), and therefore, the laser beam β is partially blocked. That is, the height of the continuous layered formation W as viewed from the light emission part of the sensor 51 (52) is the height h3 including the height of the raised glue joint section G in appearance, and the sensor 53(54) receives the laser beam β with the height h2 being reduced or decreased by the dimension Δh=h3−h1. Therefore, the height h2 of the laser beam β entering the receiving part of the sensor 53 is smaller than 20.5 mm (FIG. 5(A)) or 17.5 mm (FIG. 6(A)) by the dimension Δh, and the quantities of light received by the sensor 53 (54) are reduced in the rate Δh/[H−h1], in comparison with the quantities of light in normal conditions. The memory part of the control unit 70 stores the quantities of light thus varied in the sensor 53 (54), as being the measured values.

In this embodiment, a value corresponding to approximately 10% of the prescribed or targeted height h1 of the continuous layered formation W (the height h1 is equal to the thickness t of the gypsum board) is set to be a criterion for detecting an abnormal reduction in the height Δh=h3−h1 (i.e., occurrence of the glue-joint failure). That is, the control unit 7 is so set as to determine occurrence of the glue-joint failure when the condition is satisfied that Δh is equal to or greater than the value of approximately h1×0.1 (approximately 10% of the value h1), i.e., when the reduced dimension Δh in the height of the laser beam β is equal to or greater than approximately 0.95 mm (FIG. 5(A)) or 1.25 mm (FIG. 6(A)). For this determination, the control unit 70 sets the quantity of light equal to 90% of the quantity of light received in the normal condition by the sensor 53 (54), as being the threshold. Further, the control unit 70 stores this value of the quantity of light in the memory part, and when the quantity of light measured by the sensor 53 decreases down to the value equal to or smaller than the value of 90%, the control unit 70 determines occurrence of the glue joint failure.

FIGS. 7 to 11 are graphic diagrams (time charts) showing examples of change in the quantities of light of the laser beam β. The graphic diagrams as shown in FIGS. 7 to 11 are visually displayed on a screen of the touch panel display device 71 (FIG. 4). In FIGS. 7 to 11, the ordinate represents the light receiving rate η and the shielded rate λ of the laser beam β detected by the receiving part of the sensor 53, 54. The light receiving rate η is a value of a ratio of the measured value/the reference value, and the shielded rate λ is a ratio of 1−the measured value/the reference value. These values are closely related to the value of Δh. Further, the abscissa is a time axis. The sensors 51, 53 on the upstream side and the sensors 52, 54 on the downstream side are spaced apart a distance X in the conveyance direction from each other, and therefore, the time interval ΔT between the timing T1 and the timing T2 is defined by the distance X and the conveying velocity of the belt conveyer device 40, wherein the timing T1 is the timing for detecting a certain portion of the continuous layered formation W by the sensors 51, 53 on the upstream side and the timing T2 is the timing for detecting the same portion of the continuous layered formation W by the sensors 52, 54 on the downstream side.

Figure 7:
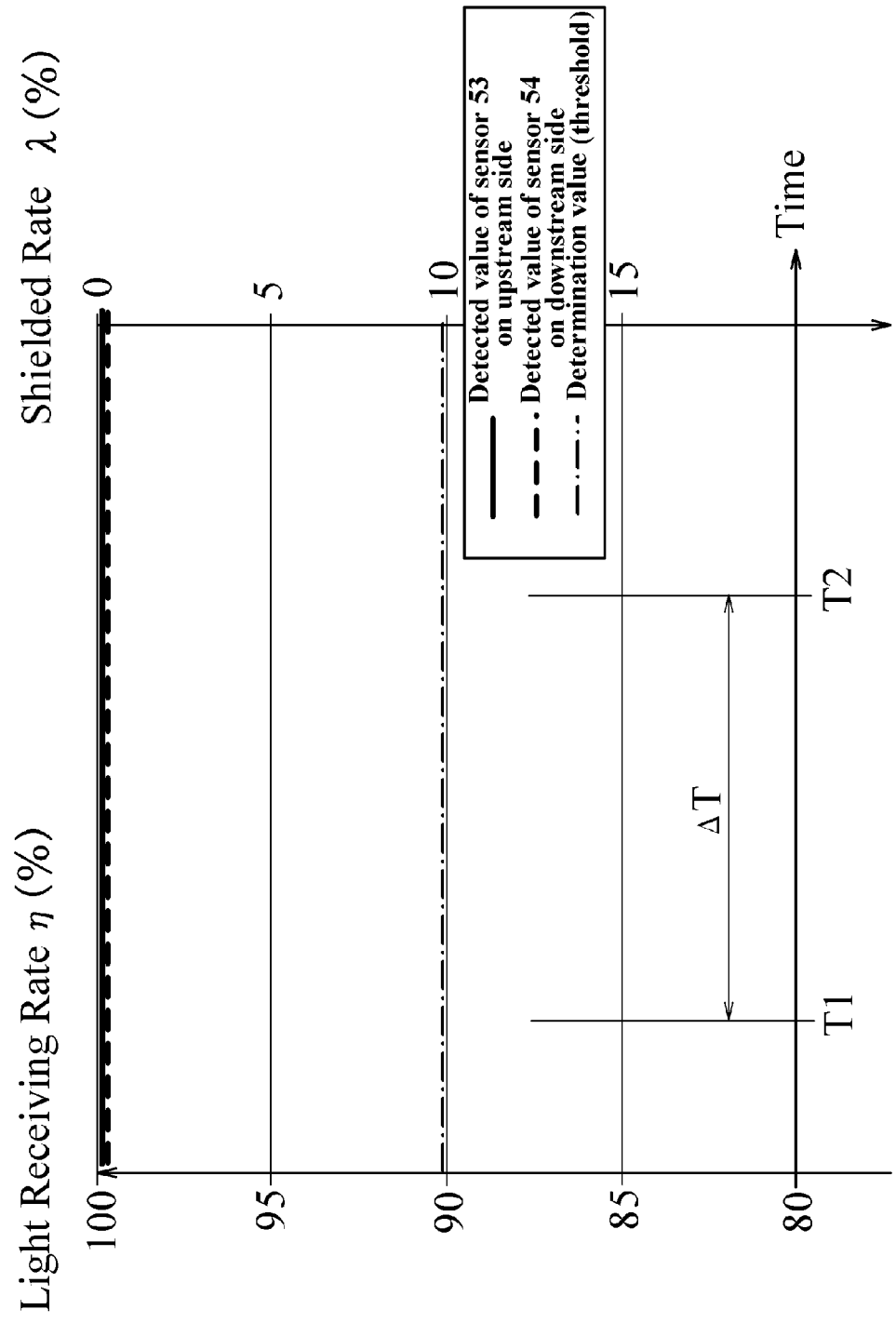
FIG. 7 is a graphic diagram (time chart) exemplifying change in a light receiving rate and a shielded rate of a laser beam, wherein a condition is shown in that the glue-joint failure does not occur at all.

In FIG. 7, there is shown a condition in that the glue-joint failure does not occur in the continuous layered formation W at all, i.e., the condition in that the sensors 53, 54 detect the quantity of light corresponding to the reference value. This is the state of Δh=0, which means that the glue joint failure does not occur in the continuous layered formation W at all. In such a condition, the control unit 70 does not cause the electronic sound alarm 72 to operate, and therefore, the alarm 72 does not sound the alarm.

Figure 8:
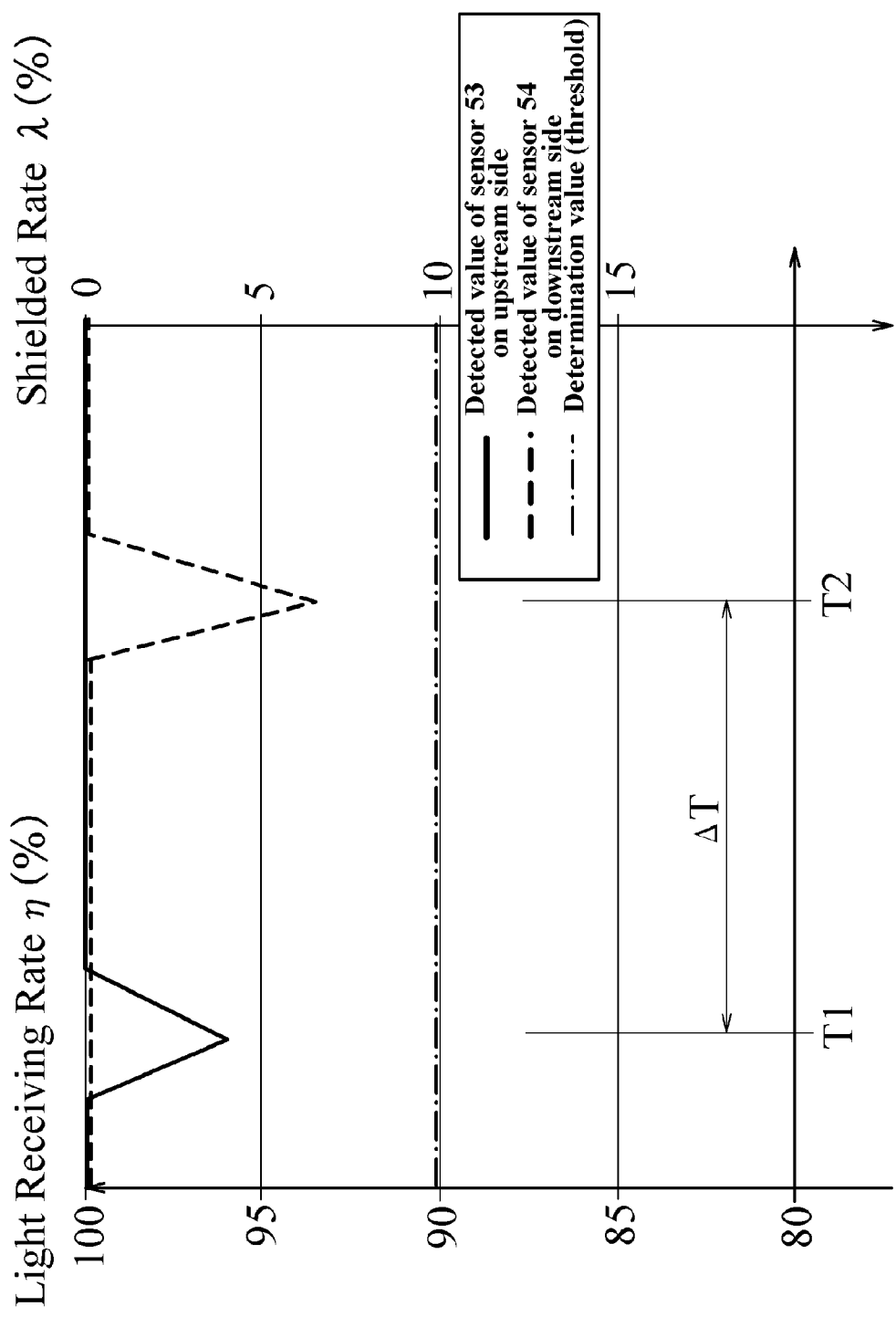
FIG. 8 is a graphic diagram (time chart) exemplifying change in the light receiving rate and the shielded rate of the laser beam, wherein a condition is shown in that an irregularity or unevenness appears on the edge portion of the continuous layered formation, but it does not fall under the glue joint failure.

In FIG. 8, there is shown a condition in that irregularity, unevenness or the like slightly occurs in the edge portion of the continuous layered formation W, but it is considered to be in a measurement error range or in a permissible range, and therefore, it is regarded as being a state in which the glue joint failure does not occur. In this condition, the regular gypsum board products are produced successively. That is, the sensors 53, 54 detect the quantities of light exceeding 0.9×the reference value (the light receiving rate η exceeds 0.9 (90%)), and it is considered that the condition of Δh smaller than h1×approximately 0.10 is maintained. In such a condition, the comparison and discrimination part of the control unit 70 does not determine occurrence of the glue joint failure, and the control unit 70 does not cause the alarm 72 to operate, and therefore, the alarm 72 does not sound the alarm.

Figure 9:
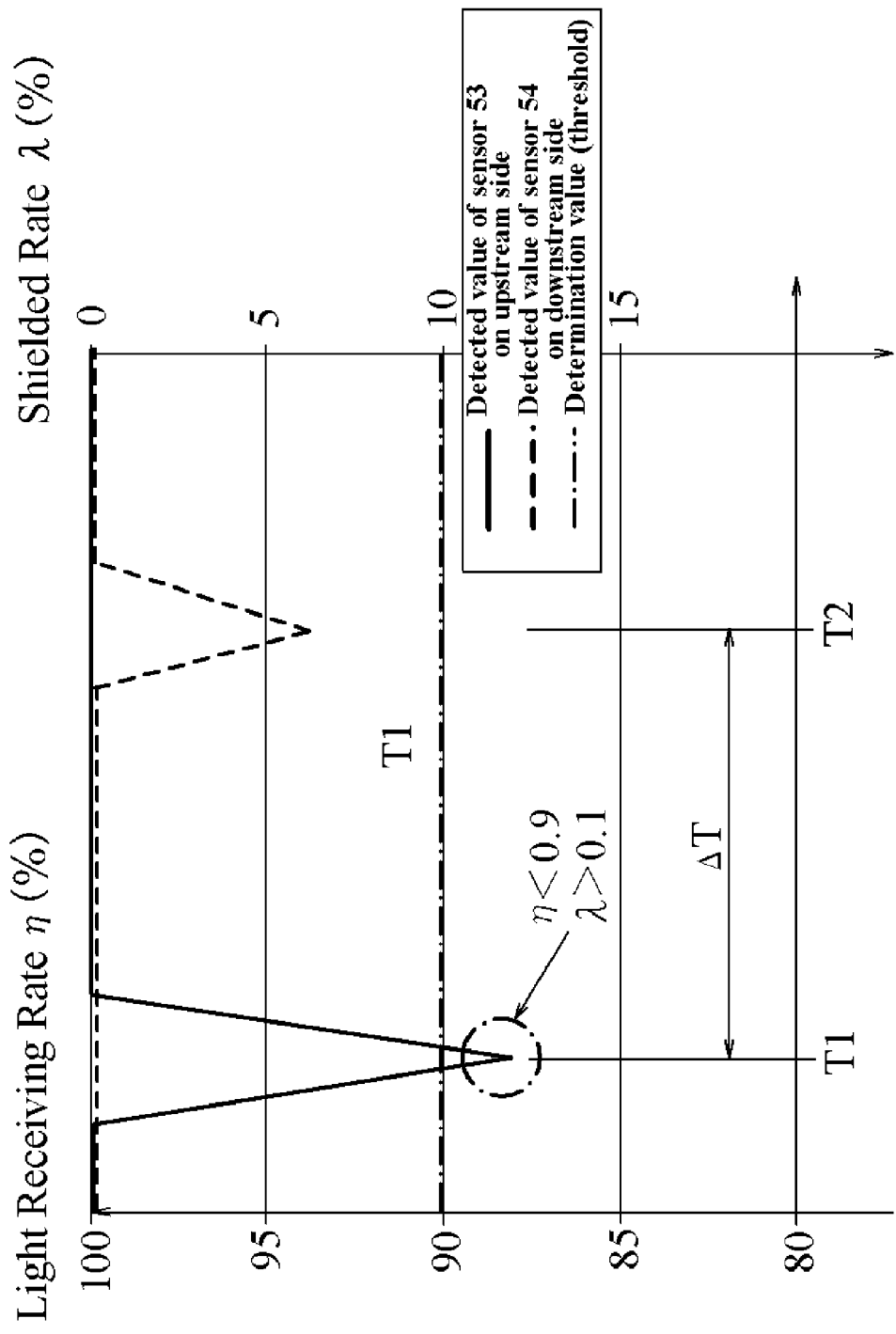
FIG. 9 is a graphic diagram (time chart) exemplifying change in the light receiving rate and the shielded rate of the laser beam, wherein a condition is shown in that the glue-joint failure happens immediately after gluing.

In FIG. 9, there is shown a condition in that the sensor 53 detects the quantities of light equal to or less than 0.9×the reference value (the light receiving rate η is equal to or less than 0.9 (90%)), but the sensor 54 detects the quantities of light exceeding 0.9×the reference value (the light receiving rate η exceeds 0.9 (90%)). A phenomenon, in which such different quantities of light are detected, is observed when the exfoliation K (FIG. 12) is created immediately after application of the glue, but the rising of the exfoliation K gets smaller as the drying and setting of the slurry S progresses. In such a condition, since the value of Δh is equal to or greater than h1×approximately 0.10 immediately after application of the glue, it may be considered that the glue-joint failure occurs in the continuous layered formation W, and therefore, the control unit 70 causes the alarm 72 to operate so as to sound the alarm for an alert warning of occurrence of the glue joint failure to the operators and so forth. Alternatively, when such variation in the quantities of light is observed, it may be considered that the glue joint failure does not occur since the glue joint failure, which occurs immediately after application of the glue, is naturally eliminated.

Figure 10:
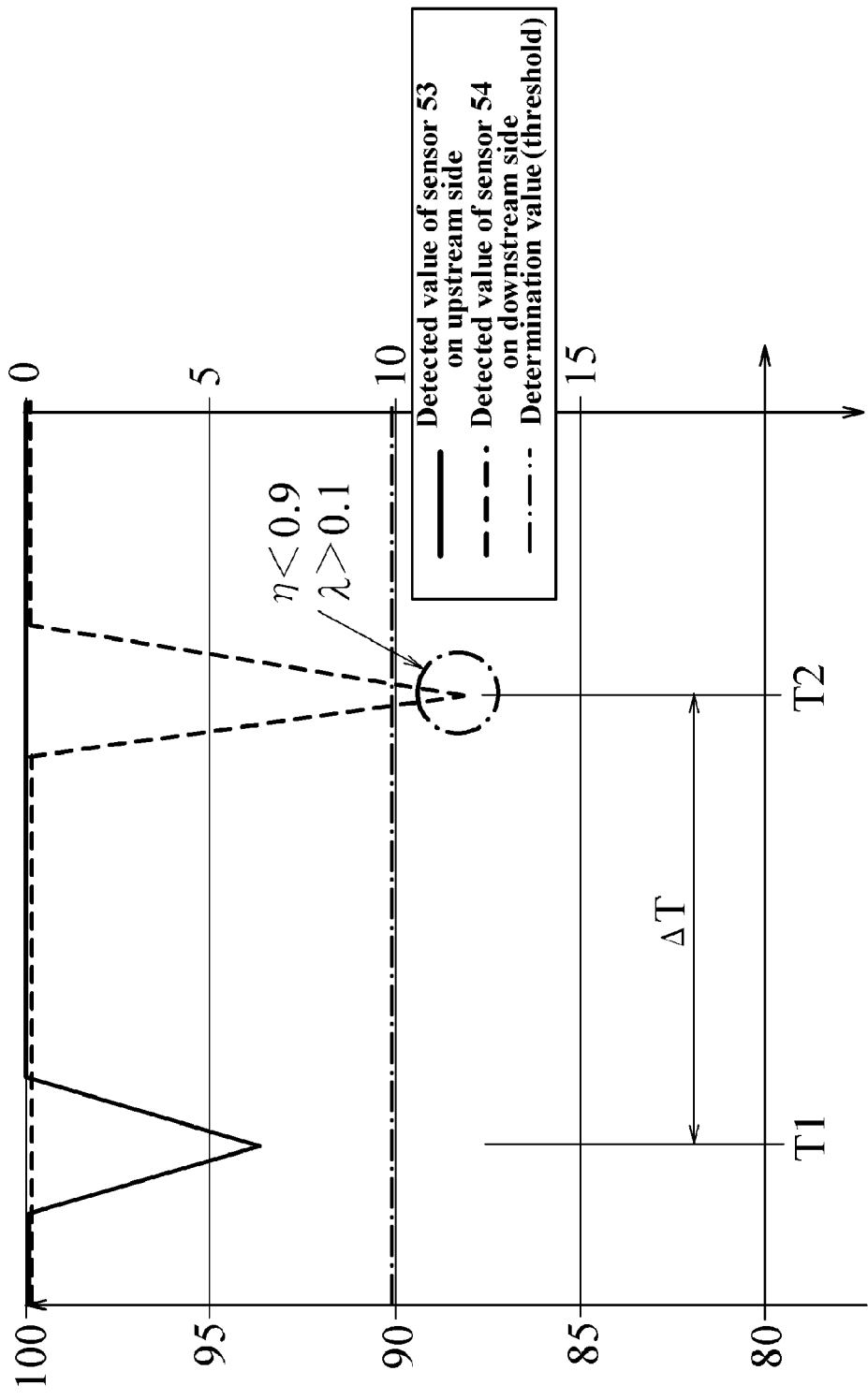
FIG. 10 is a graphic diagram (time chart) exemplifying change in the light receiving rate and the shielded rate of the laser beam, wherein a condition is shown in that the glue-joint failure happens in a conveyance process of the continuous layered formation.

In FIG. 10, there is shown a condition in that the sensor 54 detects the quantities of light equal to or less than 0.9×the reference value (the light receiving rate η is equal to or less than 0.9 (90%)), but the sensor 53 detects the quantities of light exceeding 0.9×the reference value (the light receiving rate η exceeds 0.9 (90%)). A phenomenon, in which such different quantities of light are detected, is observed when the glued state is normal immediately after application of the glue, but the exfoliation K (FIG. 12) is created as the drying and setting of the slurry S progresses; or otherwise, when the small exfoliation K created immediately after application of the glue enlarges as the drying and setting of the slurry S progresses. In such a condition, since the value of Δh is equal to or greater than h1×approximately 0.10 on the forming belt 40, it may be considered that the glue-joint failure occurs in the continuous layered formation W, and therefore, the control unit 70 causes the alarm 72 to operate so as to sound the alarm for an alert warning of occurrence of the glue joint failure to the operators and so forth.

Figure 11:
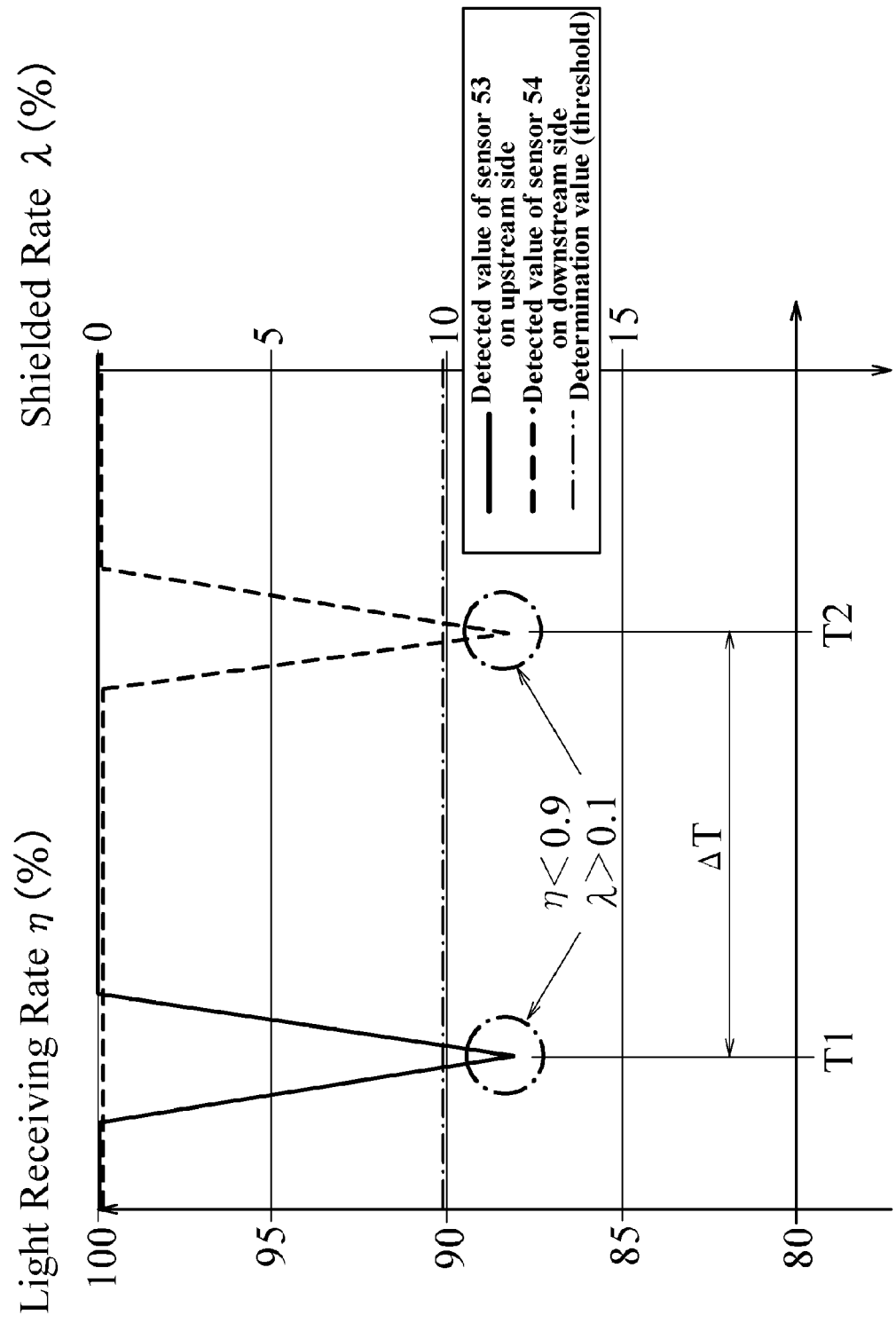
FIG. 11 is a graphic diagram (time chart) exemplifying change in the light receiving rate and the shielded rate of the laser beam, wherein a condition is shown in that the glue joint failure happens immediately after gluing and the failure is still detected in the conveyance process of the continuous layered formation.

In FIG. 11, there is shown a manner of the typical glue-joint failure, wherein the exfoliation K (FIG. 12) is created immediately after application of the glue, and the exfoliation K remains without diminishing in the drying and setting process of the slurry S. That is, both of the sensors 53, 54 detect the quantities of light equal to or less than 0.9×the reference value (the light receiving rate η is equal to or less than 0.9 (90%)). The control unit 70 causes the alarm 72 to operate so as to sound the alarm for an alert warning of occurrence of the glue-joint failure to the operators and so forth.

The control unit 70 continuously displays the detected results of the sensors 53, 54 on the display screen of the display device 71, and the operators and so forth can recognize the occurrence of the glue-joint failure by the warning sound of the alarm 72, immediately after the failure happens. When the operator recognizes the warning sound, the operator confirms the manner and degree of the glue joint failure on the basis of the indication on the display screen of the display device 71, and adjusts the supply amount of the glue in the glue supply device 21 of the gluing device 20 for overcoming the glue-joint failure condition.

As the sensors 51, 53, Digital Laser Sensor LV-300H made by Keyence Corporation and so forth may be preferably employed. As the programmable logic controller (PLC) constituting the control unit 70, a sequencer of MELSEC-Q series made by Mitsubishi Electric Corporation and so forth may be preferably employed. Further, a touch panel display device of VT-3 series made by Keyence Corporation and so forth may be preferably employed as the display device 71, and a signal phone made by Patlite Corporation and so forth may be preferably employed as the alarm 72.

The operation of the gypsum board production apparatus having the system 50 as set forth above is described hereinafter.

As shown in FIGS. 2 and 3, the supply of the lower sheet 1 is carried out in the conveyance direction of the conveyor device 40, and the mixer 3 feeds the slurry S onto the sheet 1 continuously. The scores are formed on the right and left edge portions of the sheet 1 by the scoring device (not shown), and the edge portions are folded upward by the guide members 5. The upper sheet 2, to which the glue is applied or coated by the gluing device 20, is overlaid on the lower sheet 1 and the slurry S. The sheets 1, 2 and the slurry S are pressed and formed to be the continuous three layered formation W, by means of the surface plates 8 and the forming device 30. The continuous layered formation W exiting the gate 34 of the forming device 30 is continuously conveyed by the upper belt track 41 of the forming belt 40, and the setting reaction of the slurry S proceeds during conveyance. The continuous layered formation W is roughly severed by the roughly severing rollers 45, 46 and then, the following drying step and cutting step are carried out as final steps for producing the gypsum board products.

The system 50 is always in operation during production of the gypsum boards, and the sensors 51, 52 always emit the laser beams β which traverse the continuous layered formation W. The sensors 53, 54 always receive the laser beams β and output the detected results of the quantities of light of the laser beams (3 to the arithmetic and control part in the control unit 70. The control unit 70 causes the display device 71 to display the values and graphs of the light receiving rate η (and the shielded rate λ) on its screen, on the basis of the detected results of the sensors 53, 54.

The control unit 70 determines whether the glue-joint failure occurs, on the basis of the light receiving rate η (or the shielded rate λ) obtained by the detected results of the sensors 53, 54, at a predetermined time interval (the time interval corresponding to the control cycle time).

When the control unit 70 determines that the glue-joint failure occurs, it operates the alarm 72, whereby the alarm 72 generates the warning sound for alarming the occurrence of the glue-joint failure to the operators and so forth. The operator confirms the manner and degree of the glue joint failure on the basis of the indication on the display screen of the display device 71, and adjusts the supply amount of the glue in the glue supply device 21 of the gluing device 20 in order to eliminate the glue-joint failure condition.

According to the system 50 as set forth above, the occurrence of the glue joint failure can be detected at a plurality of positions spaced apart in the conveyance direction of the continuous layered formation W, and therefore, the system 50 can detect the glue joint failure which occurs in such a manner that separation of the glued section and so forth appears on the forming belt 40. Thus, the system 50 can surely detect the glue-joint failure. Further, in the arrangement of the system 50, the glue-joint failure can be detected in arbitrary positions suitable to the production process by the sensors 51-54 located in appropriate positions of the production line. In addition, it is possible to detect the glue-joint failure in three or more positions by increasing the number of sensors. Thus, significant advantages can be obtained from practical and economical viewpoints.

Further, defects of the glue-joint condition can be surely detected at an early stage by optimizing the detecting position and the number of locations thereof, whereby the yield of production can be improved and the production loss can be reduced. According to the experiment of the present inventor, the ratio of defective products deriving from the glue-joint failure (the ratio of the defective products to the products produced in a certain period of time) can be reduced to be approximately a 100th (¹⁄₁₀₀) by employment of the system 50, and therefore, the yield rate can be significantly improved. Thus, the employment of the system 50 with the aforementioned arrangement is very effective in improvement of the productivity of the gypsum boards.

In recent years, demand of the gypsum boards with high density or the light-weight gypsum boards tend to increase. In production of such gypsum boards, a sheet of paper having a large thickness and a large basis weight is used as the sheet 1. For instance, the thickness and the basis weight of the sheet 1 used for production of the standard gypsum board are approximately 0.19-0.21 mm and approximately 100-200 g/m$^2$. On the other hand, as regards the sheet 1 used for production of the gypsum board with high density or the light-weight gypsum board, the thickness of paper is approximately 0.34-0.36 mm, and the basis weight of paper is approximately 170-300 g/m$^2$, and preferably, approximately 200-300 g/m$^2$, and more preferably, approximately 230-250 g/m$^2$. Therefore, the lower sheets of paper used for production of such gypsum boards are apt to cause warpage. Further, in production of the gypsum boards with high density, the unsolidified slurry with high density tends to push up the folded section of the sheet 1 upward, whereby the upper sheet 2 is apt to be raised. For such paper qualities peculiar to the gypsum boards with high density and behavior or properties of the slurry with high density, troubles of the glue-joint failures tend to be caused relatively frequently in the production of the gypsum boards with high density. According to the research of the present inventor, the glue joint failures occurring in the production processes of the gypsum boards with high density or the light-weight gypsum boards are, in many cases, caused in such a manner that the lower and upper sheets are temporally joined immediately after application of the glue thereto but the exfoliation of the glue-joint section happens during transportation by the forming belt 40. The glue-joint failure occurring in such a manner is not able to be detected by the conventional system for detecting the glue-joint failure. However, the system 50 with the aforementioned arrangement can surely detect the glue-joint failure in such a manner, as shown in FIG. 10, and therefore, it is very advantageous.

Preferred embodiments or examples of the present invention have been described in detail, but the present invention is not limited thereto. A variety of variations can be implemented or a variety of changes can be made in the scope of the invention as set forth in the claims.

For example, the value of the light receiving rate equal to 0.9 (90%) is employed as the threshold for discriminating the occurrence of the glue joint failure, in the aforementioned embodiment, but the threshold may be appropriately changed in accordance with the structure of the gypsum board production apparatus, the sort of the gypsum board, and so forth.

Further, in the aforementioned embodiment, the occurrence of the glue joint failure is determined when the sensor 53 on the upstream side detects the light receiving rate equal to or less than the reference value×0.9 (light receiving rate η equal to or less than 0.9 (90%)) and the sensor 54 on the downstream side detects the light receiving rate exceeding the reference value×0.9 (light receiving rate η exceeding 0.9 (90%). However, it is possible to determine that the glue joint failure does not occur in such a case, supposing that the glue-joint failure naturally disappears as the drying and setting of the slurry S progresses.

Furthermore, in the aforementioned embodiment, two sets of the detecting equipment system (the laser light emitting sensor and the laser light receiving sensor) are provided in the upstream area and the downstream area of the gypsum board production apparatus, but three or more sets of the detecting equipment system may be provided on the apparatus.

Further, in the aforementioned embodiment, the control system arranged to discriminate the occurrence of the glue joint failure on the basis of the light receiving rate is described. However, the present invention is not limited thereto, but it is possible to fix an abnormal value, thereby sensing or discriminating the occurrence of the glue-joint failure with use of a common threshold, regardless of difference in thickness of the gypsum board. For instance, it is possible to determine the occurrence of the glue joint failure when a reduction value $\Delta h$ of the height h2 of the laser beam β received by the sensors 53, 54 exceeds the permissible maximum value $\Delta h_{max}$ of the reduction value $\Delta h$, wherein the reduction value $\Delta h$ is measured and the permissible maximum value $\Delta h_{max}$ is set to be the common threshold.

In addition, the system 50 in the aforementioned embodiment uses the laser beam β having the horizontal optical axis perpendicular to the conveyance direction of the conveyance direction, but the laser beam β may be oriented in a direction inclined at a predetermined angle with respect to the conveyance direction.

Further, in the aforementioned embodiment, production of the gypsum boards having thicknesses of 9.5 mm and 12.5 mm is exemplified. However, the present invention is not limited thereto, but the present invention can be applied to production of the gypsum boards of various thicknesses, such as 6 mm, 15 mm, 18 mm, 21 mm and 25 mm.

INDUSTRIAL APPLICABILITY

The present invention is applied to the system and method for detecting the glue-joint failure, which is provided on the gypsum board production apparatus and which detects the glue-joint failure at the glue joint section of the upper and lower sheets of paper for gypsum board liner with use of the optical detection means, wherein the gypsum board production apparatus is arranged to glue the edge portions of the sheets with the gypsum slurry being held between the sheets, thereby forming the continuous layered formation, which has the cross-section of the edge portion of the gypsum board formed by gluing and which is conveyed by the forming belt.

According to the present invention, the system and method for detecting the glue-joint failure can surely detect the glue-joint failure of the upper and lower sheets at an early stage with a simple arrangement, and which allows a plurality of detecting equipment systems to be relatively easily provided in positions of the gypsum board production line spaced apart a distance in the conveyance direction of the continuous layered formation, and therefore, the advantage of the present invention is remarkable in practice.

LIST OF REFERENCE NUMERALS 1 lower sheet of paper for gypsum board liner
2 upper sheet of paper for gypsum board liner
3 mixer
8 surface plates
20 gluing device
21 glue supply device 30 gypsum board forming device
40 forming belt
41 upper belt track
42 lower belt track
45, 46 roughly severing device
50 system for detecting glue-joint failure
51, 52 laser light emitting sensor
53, 54 laser light receiving sensor
60 machine frame
70 control unit
71 touch panel display device
72 electronic sound alarm
B gypsum board
C gypsum core
E edge portion
G glue-joint section
K exfoliation or gap
S slurry
W continuous layered formation
X distance
t thickness
h height
Δh reduction value of height
α edge angle
β visible semiconductor laser beam

The invention claimed is:

1. A system for detecting glue-joint failure, which is provided on a gypsum board production apparatus and which detects the glue-joint failure at a glue joint section of upper and lower sheets of paper for gypsum board liner with use of optical detection means, wherein the gypsum board production apparatus is arranged to glue edge portions of the sheets with gypsum slurry being fed between the sheets, thereby forming a continuous layered formation, which is formed with a cross-section of an edge portion of a gypsum board and which is conveyed by a forming belt, comprising:
 a light emission part which is located on one side of said continuous layered formation on said forming belt and which projects a laser light toward an edge portion of said formation, the laser light extending in a direction intersecting a conveyance direction of the forming belt and said formation being in a drying and setting process of the slurry;
 a light receiving part which is opposed to the light emission part and located on the opposite side of said formation and which receives the laser light of the light emission part; and
 a control device for determining occurrence of the glue-joint failure when a height of said laser light blocked by said formation exceeds a predetermined value or a predetermined rate,
 wherein said laser light is so positioned that the laser light at least partially passes through an area above an upper surface of said formation and is partially blocked by rising of the edge portion of the formation.

2. The system as defined in claim 1, wherein the plurality of light emission parts are in positions spaced apart from each other in the conveyance direction of said forming belt, and the plurality of light receiving parts are in positions spaced apart from each other in the conveyance direction of said forming belt.

3. The system as defined in claim 1, wherein said laser light has a horizontal optical axis perpendicular to the conveyance direction of said forming belt.

4. The system as defined in claim 1, wherein said control device sets a quantity of light to be received in a normal condition by said light receiving part, as being a reference value, and determines occurrence of the glue-joint failure by comparing the reference value and the quantity of light detected by the light receiving part.

5. The system as defined in claim 1, wherein a quantity of light to be received in a normal condition by said light receiving part is preset on the basis of a thickness of the gypsum board to be produced, before a start of production of the gypsum board, or initially set or reset on the basis of the quantity of light constantly detected by the system, after the start of production of the gypsum board.

6. The system as defined in claim 1, wherein said control device has an arithmetic and control part which controls operation of the light emission part and the light receiving part and which receives a detected result of the light receiving part to compute the measured value of the quantity of received light;
 a memory part which memorizes the quantity of light to be received in a normal condition by the light receiving part, as being a reference value, and which memorizes a threshold for discriminating the occurrence of the glue-joint failure;
 a comparison and discrimination part which compares said measured value and said reference value to determine the occurrence of the glue-joint failure; and
 means for providing or giving a visual display or a warning of the occurrence of the glue-joint failure when the comparison and discrimination part determines the occurrence of the glue-joint failure.

7. A method for detecting glue-joint failure at a glue joint section of upper and lower sheets of paper for gypsum board liner with use of optical detection means, wherein the optical detection means is provided on a gypsum board production apparatus arranged to glue edge portions of the sheets with gypsum slurry being fed between the sheets, thereby forming a continuous layered formation, which is formed with a cross-section of an edge portion of a gypsum board and which is conveyed by a forming belt, comprising steps of:
 projecting a laser light extending in a direction intersecting a conveyance direction of the forming belt, toward the edge portion of said formation which is in a drying and setting process of the slurry, by means of a light emission part located on one side of the formation on said forming belt;
 positioning said laser beam so that the laser light at least partially passes through an area above an upper surface of said formation and is partially blocked by rising of the edge portion of the formation;
 receiving the laser light of said light emission part by means of a light receiving part which is opposed to the light emission part and located on the opposite side of said formation; and
 measuring a quantity of light received by said light receiving part and determining occurrence of the glue-joint failure on the basis of whether the quantity of light decreases by at least a predetermined value or a predetermined rate.

8. The method as defined in claim 7, including steps of positioning the plurality of light emission parts in positions spaced apart from each other in the conveyance direction of said forming belt, positioning the plurality of light receiving parts in positions spaced apart from each other in the conveyance direction of the forming belt, and projecting the laser lights to said continuous layered formation, each having a horizontal optical axis, in an upstream area and a downstream area of the forming belt.

9. The method as defined in claim 7, wherein a quantity of light received by said light receiving part is input into a control device as being a measured value, the quantity of light to be received in a normal condition by the light receiving part is set to be a reference value, the measured value of the quantity of light detected by the light receiving part is compared with the reference value by the control device, and a visual display or a warning of the occurrence of the glue-joint failure is provided or given by display means or warning means of the control device, when a rate of the measured value to said reference value decreases down to a predetermined rate or less.

10. The method as defined in claim 9, wherein said predetermined rate is set to be in a range from 95% to 85%.

11. The method as defined in claim 8, wherein a visual display or a warning of the occurrence of the glue-joint failure is provided or given by display means or warning means, when the occurrence of the glue-joint failure is determined on the basis of the quantity of light detected by at least one of said light receiving parts.

12. The method as defined in claim 8, wherein a visual display or a warning of the occurrence of the glue-joint failure is provided or given by display means or warning means, when the occurrence of the glue-joint failure is indicated by every result which is determined on the basis of the quantities of light detected by said light receiving parts.

13. The method as defined in claim 9, wherein the quantity of light constantly received by said light receiving part after a start of production of the gypsum board is set to be said reference value.

14. The method as defined in claim 9, wherein said reference value is preset on the basis of a thickness of the gypsum board before a start of production of the gypsum board.

15. An apparatus for producing gypsum boards having the system as defined in claim 1.

16. The apparatus as defined in claim 15, which has a lower sheet feeding device for feeding of said lower sheet having a basis weight in a range from 170 $g/m^2$ to 300 $g/m^2$.

17. A method for producing gypsum boards with use of the method as defined in claim 7.

18. The method as defined in claim 17, wherein said gypsum board is produced by using said lower sheet with a basis weight in a range from 170 $g/m^2$ to 300 $g/m^2$, as a raw material.

19. The method as defined in claim 17, wherein the gypsum board with high density is produced, which has a specific gravity equal to or greater than 0.9, or wherein the gypsum board with low density is produced, which has a specific gravity equal to or less than 0.6.

* * * * *